United States Patent [19]

Kamm et al.

[11] Patent Number: 4,671,105

[45] Date of Patent: Jun. 9, 1987

[54] PROCESS AND DEVICE FOR DETERMINING THE INTERNAL CONDITION OF TREES OR WOODEN COMPONENTS

[76] Inventors: Willibald F. G. Kamm, Paul-Bähr-Str.1; Siegfried Voss, Auf dem Hamfelde 5, both of Bad Oeynhausen 4970, Fed. Rep. of Germany

[21] Appl. No.: 820,738

[22] Filed: Jan. 17, 1986

[30] Foreign Application Priority Data

Jan. 22, 1985 [DE] Fed. Rep. of Germany ....... 3501841

[51] Int. Cl.[4] ..................... G01N 3/42; G01N 33/46
[52] U.S. Cl. ........................................... 73/81; 73/85
[58] Field of Search ............. 73/81, 85, 432 Z, 432 R, 73/432.1, 866

[56] References Cited

U.S. PATENT DOCUMENTS

| 2,030,855 | 2/1936 | Canfield | 73/81 X |
|---|---|---|---|
| 2,389,030 | 11/1945 | Dana | 73/81 |
| 2,752,591 | 6/1956 | Felbeck et al. | 73/85 |
| 3,379,052 | 4/1968 | Howard et al. | 73/81 |
| 3,894,588 | 7/1975 | Brill | 73/85 X |
| 4,059,990 | 11/1977 | Glover et al. | 73/81 |
| 4,111,039 | 9/1978 | Yamawaki et al. | 73/81 |
| 4,249,414 | 2/1981 | Barth | 73/85 X |
| 4,343,179 | 8/1982 | Åström et al. | 73/81 |

FOREIGN PATENT DOCUMENTS

| 1067615 | 10/1959 | Fed. Rep. of Germany | 73/81 |
|---|---|---|---|
| 2638261 | 3/1977 | Fed. Rep. of Germany | 73/81 |
| 44182 | 2/1961 | Poland | 73/81 |
| 157145 | 11/1962 | U.S.S.R. | 73/81 |
| 912827 | 3/1982 | U.S.S.R. | 73/81 |
| 1158892 | 5/1985 | U.S.S.R. | 73/81 |

OTHER PUBLICATIONS

"Is Wood Hardness Affected by Preservative Treatment?"; *Forest Products Journal;* vol. 22, No. 5, May 1972; pp. 60–61; Robert L. Ethington.
"Erfahrungen mit einem Gerät zur Fäuleermittlung an Stehenden Stämmen"; *Forstw. Cbl.;* vol. 81; published 1962, issue 7/8; pp. 222–230; Von H. Zycha et al.

*Primary Examiner*—Stewart J. Levy
*Assistant Examiner*—Tom Noland
*Attorney, Agent, or Firm*—Salter & Michaelson

[57] ABSTRACT

The invention pertains to a process and to a device for determining the internal condition of trees or wooden components, whereby a needle is inserted into the wood, with the aim of hereby obtaining measured results more precise than possible in the past. The solution proposed is to rotate the needle, whereby the diameter of the needle head is greater than the diameter of the needle shaft, and to measure the power consumption of the needle's drive mechanisms.

8 Claims, 9 Drawing Figures

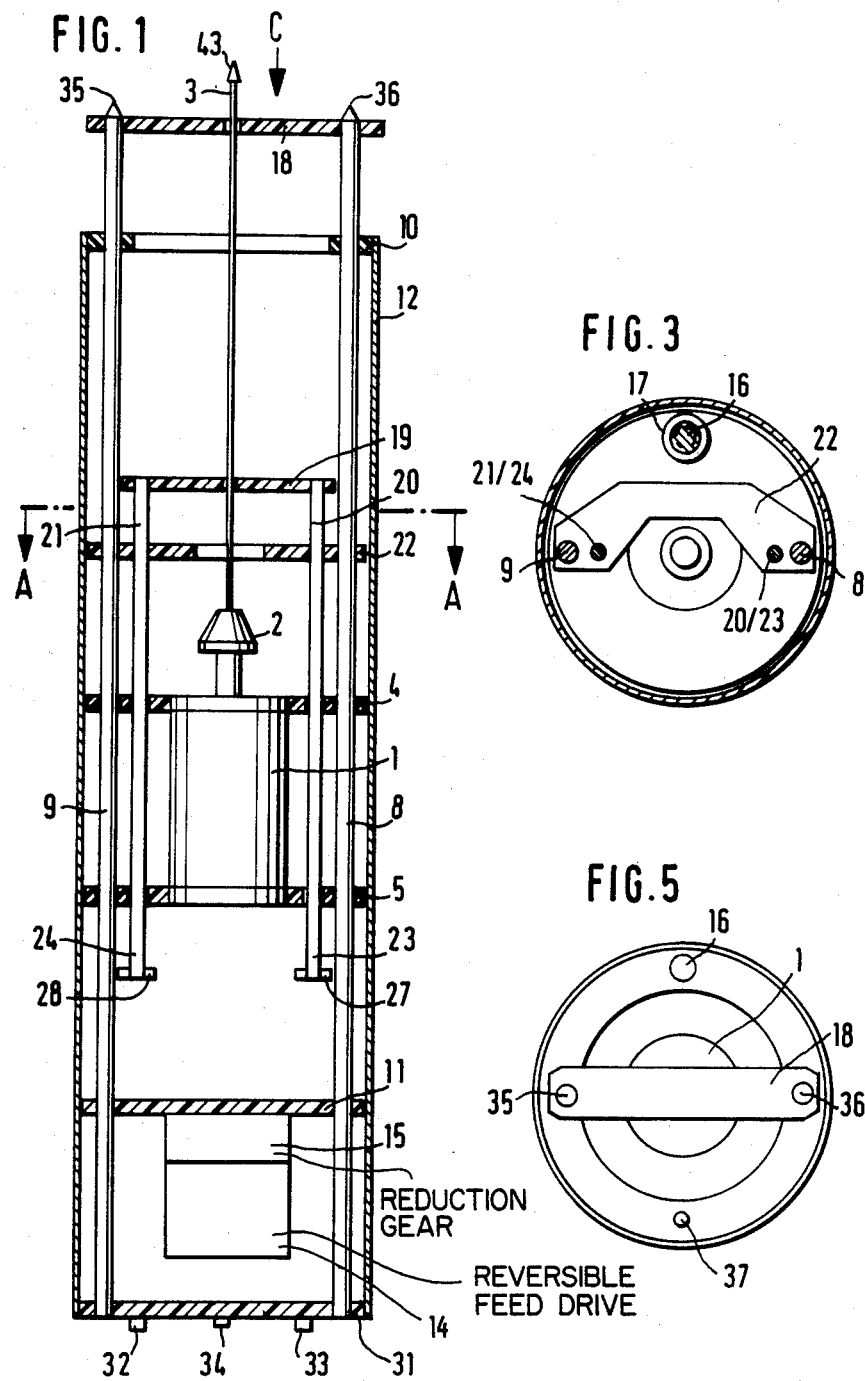

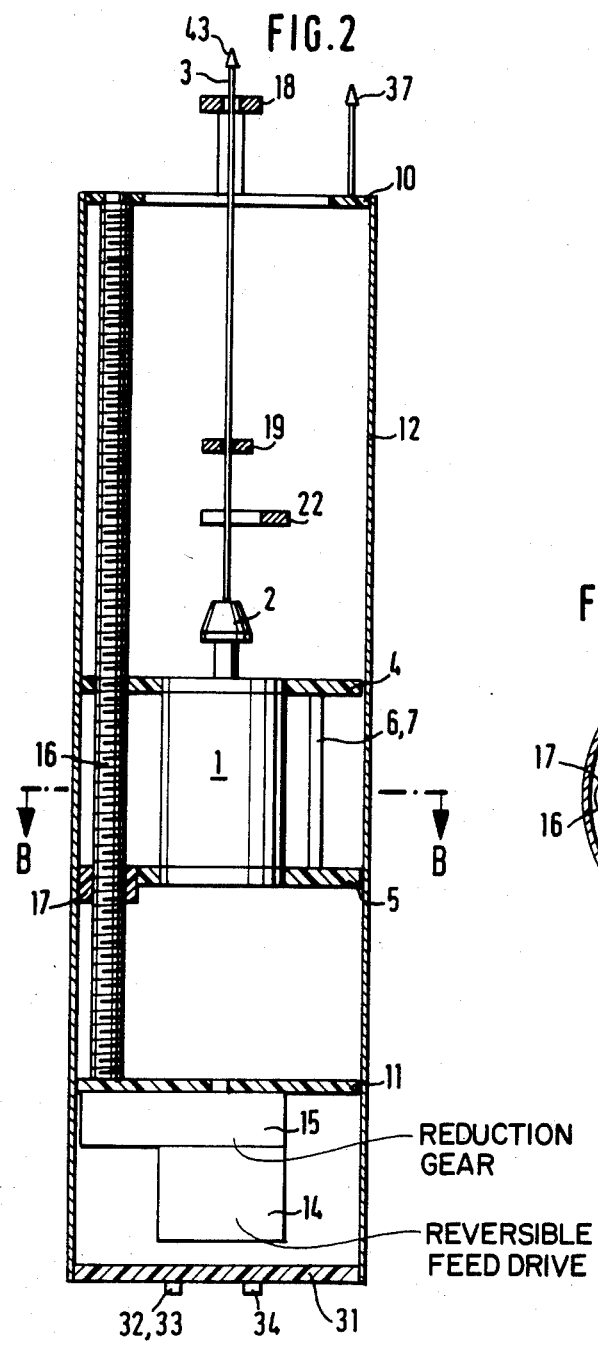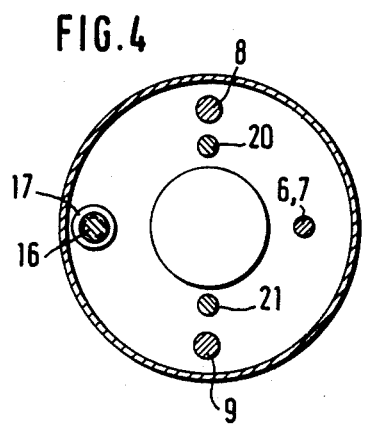

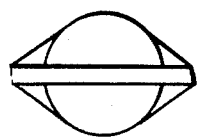
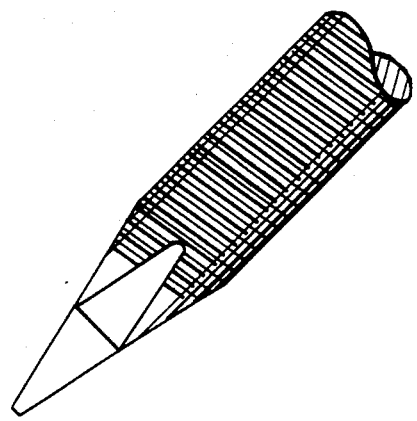
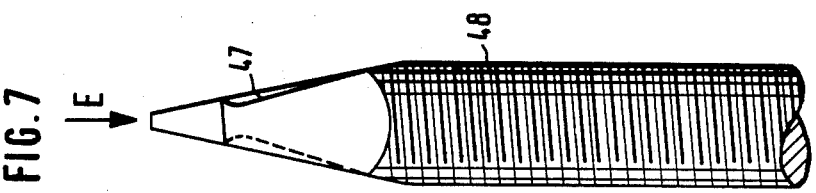
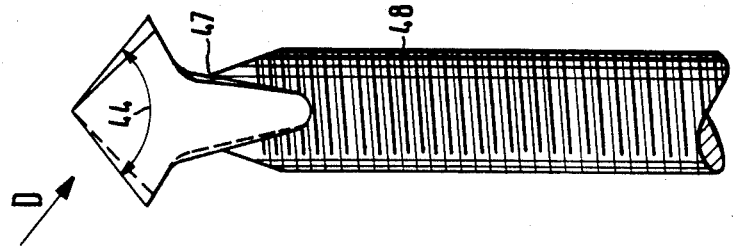

PROCESS AND DEVICE FOR DETERMINING THE INTERNAL CONDITION OF TREES OR WOODEN COMPONENTS

BACKGROUND AND SUMMARY OF THE INVENTION

The invention pertains to a process and a device for determining the internal condition of wooden structures such as trees located along roads, on plantations, in parks, or in forests, for the purpose of evaluating their state of health, as well as wooden poles or wooden components in bridges, buildings, or frame structures for potential damage caused by plant or animal pests.

In addition to the non-destructive methods utilized for determining the internal condition of trees or wooden components through the use of ultrasound, X-rays, or the like, procedures are generally known to exist in which the test object is drilled open and information is obtained about the wood's internal condition by examining the bore hole, e.g. through the use of an electric probe, or by examining the wooden material removed by drilling. Such procedures, however, are either too expensive because of equipment costs or else they result in a substantial reduction of the test object's strength characteristics.

A device and a process have already been proposed for eliminating these disadvantages, whereby a spring-loaded needle is inserted into the wood and the penetration resistance is measured on the basis of the depth of penetration (*Forstw. Cbl.*, Vol. 81, 1962, 7/8, 222–230). The results obtained from this procedure are quite imprecise, however, and permit one to make only a rough estimate about the internal condition of the test object. This is especially true as the depths of penetration become greater, since the results are falsified to the extent that the frictional contact surfaces of the needle with the wood grow larger. In spite of this, such a needle-based procedure is preferred by specialists because it causes no appreciable damage to the strength characteristics of the wood being evaluated.

The purpose of the invention is therefore to improve upon the needle-based procedure in such a way that it will produce results which are considerably more precise, while at the same time retaining its practical utility for taking measurements at reasonable cost.

As specified by the invention, this purpose is fulfilled by means of a process in which the needle is rotated, whereby the diameter of the needle's head is greater than the diameter of the needle's shaft, and where power consumption by the needle's rotary drive mechanism and/or feed drive mechanism is measured during penetration.

The process upon which the invention is based provides results which are reliable and error-free because, during insertion of the rotating needle with its somewhat enlarged head, only those forces which are analogous to the internal condition of the wood are able to act upon the head of the needle, so that the measurement of power consumption on the part of the needle's drive mechanisms provides a precise profile of the wood's inner structure, dependent to an accurate extent upon the respective position of the needle's head, i.e. the depth of the needle's penetration.

The operator is able to observe the measurement results optically, as well as acoustically based on changes in the sound of the needle's motion, so that such an operator already obtains in advance a rough indication of the wood's condition. In accordance with a practical working variant of the invention, such results can also be made visible for detailed evaluation on a screen, recorded on a moving graph, and/or stored on an electronic data carrier.

In one preferred working variant of the process upon which the invention is based, the power consumption of the needle's drive mechanisms is determined by measuring the input of electrical current by the needle's rotary drive and/or its feed drive during penetration. Consumption during idling, and thus the natural power losses of the drive mechanisms, have no influence upon the measured result.

Alternatively, power consumption by the drives can also be determined by measuring the change in the rotary speed of the rotary drive and/or the change in the forward speed of the feed drive during the needle penetration process.

It is also possible to determine power consumption by measuring the change in torque for the rotary drive and/or the change in forward thrust for the feed drive during penetration.

All of these variations of the process upon which the invention is based can be carried out with or without a constant forward speed for the needle's feed drive.

One practical device used for carrying out the procedure makes provision for a needle consisting of a steel wire with a length no greater than the maximum thickness of the test object and with a generally constant shaft diameter of less than 2 mm, whereby the head of the needle forms a flat, triangular tip possessing a rotational diameter greater than 2 mm. Excellent measurement results were obtained in initial tests using a needle having this shape, and using the process upon which the invention is based. In terms of precision, such results far surpass all of the procedures and devices previously known to exist.

If needles with a very large axial length are required, one advantageous working variant of the invention makes provision for the needle to be passed through at least one support element which is movable relative to the needle during the penetration process, such passage taking place between the fixed end of the needle and its head.

It may be practical to cut a fine thread into the surface of the needle shaft, which thread transports the chipped or pulverized wood material out of the entry channel, thus keeping the needle shaft free from frictional forces which might impair measurement results in extreme cases where the wood is very moist or in a similar condition.

DESCRIPTION OF THE DRAWINGS

One working variant of a device as specified by the invention is described in greater detail below on the basis of the drawings. Illustrated are the following:

FIG. 1 a longitudinal section through a working variant as specified by the invention;

FIG. 2 the longitudinal section for FIG. 1, rotated by 90°;

FIG. 3 section A—A for FIG. 1;

FIG. 4 section B—B for FIG. 2;

FIG. 5 frontal view C for FIG. 1;

FIG. 6 side view of the needle;

FIG. 7 side view for FIG. 6, rotated by 90°;

FIG. 8 frontal view D for FIG. 6; and

FIG. 9 frontal view E for FIG. 7.

DESCRIPTION OF THE INVENTION

FIGS. 1 and 2 indicate the rotary drive by the number 1, together with the feed mechanism 2 for easy replacement of the needle 3. The rotary drive 1 is held in place by slide rings 4, 5 and by spacing rods 6, 7, and it is guided so as to move back and forth along slide rods 8, 9. The slide rods 8, 9 are mounted on support plates 10, 11, which simultaneously function as mounts for a protective sheath 12 that encloses the entire device. Power supply for the rotary drive 1 can be effected by means of a cable as well as by way of the slide rods 8, 9. In the latter case, both the slide rings 4, 5 and the support plates 10, 11 should be manufactured of non-conductive material.

Movement back and forth by rotary drive 1 is accomplished by means of a reversible feed drive 14, a reduction gear 15, a feed screw 16 mounted on support plates 10, 11, and a threaded nut 17 placed on slide ring 4 or 5.

The needle 3 is positioned in a backrest 18 which is attached to the front support plate 10 so as to be easily replaceable and capable of receiving needles of varying diameter. A particularly advantageous form of needle 3 is represented in FIGS. 6–9 in enlarged scale. The needle consists of a break-resistant steel wire whose head 43 has been expanded by flattening to form a wedge, whereby the rotational diameter of the needle head 43 is wider than the shaft diameter of the needle. The head angle 44 of the needle's tip is larger or smaller depending upon the type of material undergoing testing; but in any case, the head 43 is devoid of screw threads as illustrated. The sides of the needle head are undercut for the sake of practicality, as shown by reference number 47. One advantageous working variant of the needle also makes provision for a fine thread or microthread 48 to be cut into the surface of the needle's shaft in order to transport chipped or pulverized wood material out of the needle's entry channel.

In order to avoid a possible vibration loop caused by needle 3 during penetration into the wood, an axially movable needle support 19 is arranged in such a way that its initial position prior to the start of the penetration process is approximately in the middle of the feed path. The needle support 19 used for guiding the needle 3 is held in place by means of guide rails 20, 21 together with spacer 22, which is positioned so as to slide along slide rods 8, 9. The spacer 22 is held together by the carrier rods 23, 24, which are mounted on the slide rings 4, 5 so as to move axially.

Upon insertion of the needle, the front slide ring 4 moves against the spacer 22 and pushes it, together with guide rails 20, 21 and needle support 19, to its final forward position, until a limit switch shuts off the feed drive 14 and the rotary drive 1. During its reverse movement the rotary drive 1 is now pulled back far enough until the posterior slide ring 5 has moved against return studs 27, 28, thus pulling the needle support 19 and its connected parts back far enough until a limit switch shuts off the return.

According to an additional working variant of the invention, not depicted here, the movement of the needle support 19 can also take place by way of a second feed screw whose rotational speed, i.e. whose pitch, has a 1:2 ratio with respect to feed screw 16; parts 23, 24, 27, 28 are then eliminated.

In order to carry out the process upon which the invention is based, the device can also be fixed manually to the test object with the aid of positioning points 35, 36, 37, which are located on the backrest 18 so that they can be moved and locked into place. If it is not desired or not possible to hold the device by hand, as when several devices are used simultaneously for conducting the test, then the possibility also exists for holding the devices in place by means of a separate hitching unit.

The electrical circuits of the rotary drive 1 are designed such that they can be operated alone, whereas the feed drive 14 is able to start only after the rotary drive 1 has been switched on. This measure is intended to prevent the needle 3 from being pushed against the test object while idle, whereby it could be bent out of shape. Switch 32 is used to switch feed drive 14 and rotary drive 1 on and off at the same time. Switch 33 is used for switching rotary drive 1 on and off independently. Switch 34 is used to control the direction of rotation for feed drive 14 during its forward and reverse motion. These switches are located on switch plate 31 at the rear of the device.

We claim:

1. A method of determining the internal condition of the wood of a wooden structure such as a tree or a wooden component, comprising inserting an elongated needle into said wooden structure, said needle having a head portion and an elongated shaft extending from said portion, said head portion being of substantially greater rotational diameter than the shaft, being substantially devoid of screw threads thereon and being forwardly tapered, said needle being mechanically driven in an axial direction by drive means external of the wooden structure and mechanically rotated by drive means external of the wooden structure to advance it into said wooden structure; and measuring the power consumed in mechanically rotating said needle as it is inserted into said wooden structure.

2. In the method of claim 1, said needle being mechanically driven in an axial direction at a substantially constant rate of speed.

3. A method of determining the internal condition of the wood of a wooden structure, such as a tree or a wooden component, comprising inserting an elongated needle into said wooden structure, said needle having a head portion and an elongated shaft extending from said head portion, said head portion being of substantially greater rotational diameter than the shaft, being substantially devoid of screw threads thereon and being forwardly tapered, said needle being mechanically driven in an axial direction by drive means external of the wooden structure and mechanically rotated by drive means external of the wooden structure to advance it into said wooden structure; and measuring the power consumed in mechanically driving said needle in an axial direction as it is inserted into said wooden structure.

4. A method of determining the internal condition of the wood of a wooden structure, such as a tree or a wooden component, comprising inserting an elongated needle into said wooden structure, said needle having a head portion and an elongated shaft extending from said head portion, said head portion being of substantially greater rotational diameter than the shaft, being substantially devoid of screw threads thereon and being forwardly tapered, said needle being mechanically driven in an axial direction by drive means external of the wooden structure and mechanically rotated by drive means external of the wooden structural to advance it into said wooden structure; and separately measuring both the power consumed in mechanically rotating said needle and the power consumed in axially driving said needle as it is inserted into said wooden structure.

5. A device for determining the internal condition of the wood of a wooden structure, such as a tree or a wooden component, comprising an elongated needle having a head portion and an elongated shaft extending from said head portion, said head portion being of substantially greater rotational diameter than the shaft, being substantially devoid of screw threads thereon and being forwardly tapered, means external of said wooden structure for mechanically rotating said needle; means external of said wooden structure for mechanically driving said needle in an axial direction; and means for measuring the power consumed in mechanically rotating said needle.

6. The device of claim 5 further comprising means for measuring the power consumed in mechanically driving said needle in an axial direction.

7. In the device of claim 5, said means for mechanically driving said needle in an axial direction further characterized as driving said needle at a substantially constant rate of speed.

8. A device for determining the internal condition of the wood or a wooden structure, such as a tree or a wooden component, comprising an elongated needle having a head portion and an elongated shaft extending from said head portion, said head portion being of substantially greater rotational diameter than the shaft, being substantially devoid of screw threads thereon and being forwardly tapered, means external of said wooden structure for mechanically rotating said needle; means external of said wooden structure for mechanically driving said needle in an axial direction; and means for measuring the power consumed in mechanically driving said needle in an axial direction.

* * * * *